United States Patent [19]

Schwartz et al.

[11] Patent Number: 5,298,422
[45] Date of Patent: Mar. 29, 1994

[54] MYOGENIC VECTOR SYSTEMS

[75] Inventors: Robert J. Schwartz; Franco J. DeMayo; Bert W. O'Malley, all of Houston, Tex.

[73] Assignee: Baylor College of Medicine, Houston, Tex.

[21] Appl. No.: 789,919

[22] Filed: Nov. 6, 1991

[51] Int. Cl.$^5$ ............................................. C12N 15/63
[52] U.S. Cl. ................... 435/320.1; 435/69.1; 435/172.3; 435/69.4
[58] Field of Search ....................... 435/69.1, 320.1

[56] References Cited

U.S. PATENT DOCUMENTS

| | | | |
|---|---|---|---|
| 4,783,405 | 11/1988 | Kovacevic et al. | 435/68 |
| 5,082,783 | 1/1992 | Ernst et al. | 435/69.1 |
| 5,093,317 | 3/1992 | Lewis et al. | 514/12 |

FOREIGN PATENT DOCUMENTS

| | | |
|---|---|---|
| 0174608 | 3/1986 | European Pat. Off. |
| 0336155 | 10/1989 | European Pat. Off. |
| WO91/11522 | 8/1991 | PCT Int'l Appl. |
| WO91/12329 | 8/1991 | PCT Int'l Appl. |

OTHER PUBLICATIONS

Methods in Enzymology, 185:487–511; 1990, Kaufman Vectors Used for Expression in Mammalian Cells.

Nach. Acids, Res. 14:1683–1701, 1986, Grichnik et al, Tissue restricted and stage specific transcription is maintained within 411 nucleotides flanking . . . .

G. Acsadi, et al.; Direct Gene Transfer and Expression in Cardiac and Skeletal Muscle; Ped. Res. 29 (4 part 2), 1991:126A.

A. Andreadis, et al.; Splicing of Mutually Exclusive Exons of Troponin T in Transfected Cells; Journal of Cellular Biochemistry, Alan R. Liss, Inc., New York, p. 119, L502 (1987).

H. Appelhans, et al.; Characterization of a human genomic DNA fragment coding for a myosin heavy chain; Hum. Genet., 65:198–203 (1983).

H. H. Arnold, et al.; Regulated Expression of Transfected Muscle Specific Genes; Journal of Cellular Biochemistry, Alan R. Liss, Inc., New York, p. 66, L206 (1987).

H. Aviv, et al.; Biosynthesis and Stability of Globin mRNA in Cultured Erythroleukemic Friend Cells; Cell, 495–503.

A. Baker, et al.; Cloning and expression of full-length cDNA encoding human vitamin D receptor; Proc. Natl. Acad. Sci. USA, 85:3294–3298 (1988).

E. Barr; et al.; Systemic Delivery of Recombinant Proteins by Genetically Modified Myoblasts; Science; 254:1507–1509 (1991).

D. J. Bergsma, et al.; Delimitation and Characterization of cis-Acting DNA Sequences Required for the Regulated Expression and Transcriptional Control of the Chicken Skeletal α-Actin Gene; Molecular and Cellular Biology, 6:2462–2475 (1986).

J. Boulter, et al.; Isolation and Sequence of cDNA Clones Coding for the Precursor to the γ Subunit of
(List continued on next page.)

Primary Examiner—Robert J. Hill, Jr.
Assistant Examiner—John D. Ulm
Attorney, Agent, or Firm—Fulbright & Jaworski

[57] ABSTRACT

The present invention includes a Myogenic vector system (MVS) for the expression of a nucleic acid sequence in myogenic tissue. The MVS contains a promoter, a cassette with the sequence of interest, a 3' untranslated region (3' UTR) and contiguous noncoding region (NCR). Further enhancements can include the addition of a leader sequence, intron sequence, initiation codon and specific restriction endonucleases. To facilitate uptake and myogenic expression, the MVS can be coated with histones and a DNA initiation complex composed of a serum response factor, transcription initiation factor and a transregulatory factor attached to the promoter by interaction with the serum response element and TATA box. The MVS can be used for a variety of purposes including gene replacement, vaccine production, vaccination, treatment of disease and muscle atrophy. When the MVS is injected into a myogenic system it will produce the polypeptide from the sequence of interest.

32 Claims, 9 Drawing Sheets

OTHER PUBLICATIONS

Mouse Muscle Nicotinic Acetylcholine Receptor; Jrn. of Neuroscience Research, 16:37–49 (1986).

R. L. Brinster, et al.; Factors affecting the efficiency of introducing foreign DNA into mice by microinjecting eggs; Proc. Nat. Acad. Sci. USA, 82:4438–4442 (1985).

A. Buonanno, et al.; A Universal Oligonucleotide Probe for Acetylcholine Receptor Genes; The Journal of Biological Chemistry, 261:16451–16458 (1986).

S. L. Carroll, et al.; A 29-Nucleotide DNA Segment Containing an Evolutionarily Conserved Motif Is Required in cis for Cell-Type-Restricted Repression of the Chicken α-Smooth Muscle Actin Gene Core Promoter; Molecular and Cellular Biology, 8:241–250 (1988).

D. F. Catanzaro, et al.; Human Cardiac Myosin Heavy Chain Genes, Isolation of a Genomic DNA Clone and Its Characterization and of a Second Unique Clone Also Present in the Human Genome; Circulation Research, 59:655–662 (1986).

L. Chan, et al.; Molecular Genetics of the Plasma Apolipoproteins; Molecular Biology of the Cardiovascular System, S. Chien, Ed., Lea & Febiger, Philadelphia, 10:183–219 (1990).

K. S. Chang, et al.; The complete sequence of the chicken α-cardiac actin gene: a highly conserved vertebrate gene; Nucleic Acids Research, 13:1223–1237 (1985).

K. S. Chang, et al.; Isolation and Characterization of Six Different Chicken Actin Genes; Molecular and Cellular Biology, 4:2498–2508 (1984).

P. Cheung, et al.; Nucleotide sequence of cloned cDNA of human apolipoprotein A–I; Nucleic Acids Research, 11:3703–3715 (1983).

K-L. Chow, et al.; A Combination of Closely Associated Positive and Negative cis-Acting Promoter Elements Regulates Transcription of the Skeletal α-Actin Gene; Molecular and Cellular Biology, 10:528–538 (1990).

N. E. Cooke, et al.; Human Prolactin cDNA Structural Analysis and Evolutionary Comparisons; The Journal of Biological Chemistry, 256:4007–4016 (1981).

F. M. DeNoto, et al.; Human growth hormone DNA sequence and mRNA structure: possible alternative splicing; Nucleic Acids Research, 9:3719–3730 (1981).

D. L. DeVol, et al.; Activation of insulin-like growth factor gene expression during work-induced skeletal muscle growth; American Physiological Society, E89–E95 (1990).

J. Dhawan; Systemic Delivery of Human Growth Hormone by Injection of Genetically Engineered Myoblasts; Science, 254:1509–1512 (1991).

M. J. Dobersen, et al.; Herpes Simplex Virus Type 2 Induced Pyrimidine Nucleoside Kinase: Enzymatic Basis for the Selective Antiherpetic Effect of 5-Halogenated Analogues of Deoxycytidine; Biochemistry, 17:920–928 (1978).

J. Eldridge, et al.; Nucleotide sequence of the chicken cardiac alpha actin gene: absence of strong homologies in the promoter and 3'-untranslated regions with the skeletal alpha actin sequence, Gene, 36:55–63 (1985).

R. A. Fleischman; Southwestern Internal Medicine Conference: Human Gene Therapy; The Am. Jrnl. of the Medical Sciences, 301:353–363 (1991).

J. R. Florini, et al.; Highly Specific Inhibition of IGF-I-stimulated Differentiation by an Antisense Oligodeoxyribonucleotide to Myogenin mRNA; The Journal of Biological Chemistry, 265:13435–13437 (1990).

J. R. Florini; Hormonal Control of Muscle Growth; Muscle & Nerve, 10:577–598 (1987).

J. A. Fornwald, et al.; The complete nucleotide sequence of the chick a-actin gene and its evolutionary relationship to the actin gene family; Nucleic Acids Research, 10:3861–3876 (1982).

B. A. French, et al.; Analysis of a CR1 (chicken repeat) sequence flanking the 5' end of the gene encoding α-skeletal actin; Gene, 88:173–180 (1990).

T. Friedmann; Progress Toward Human Gene Therapy; Science, 244:1275–1281 (1989).

R. I. Garver, et al.; Clonal Gene Therapy: Transplanted Mouse Fibroblast Clones Express Human α1-Antitrypsin Gene in Vivo; Science, 237:762–764 (1987).

S. C. Gehnrich, et al.; Liver (B-type) Phosphofructokinase mRNA; The Jrnl. of Biological Chemistry, 263:11755–11759 (1988).

G. Gillespie, et al.; The 3'-untranslated sequence of human skeletal muscle α-actin mRNA; Journal of Muscle Research and Cell Motility, 5:457–464 (1984).

J. W. Grant; Mammalian Nonsarcomeric Myosin Regulatory Light Chains Are Encoded by Two Differentially Regulated and Linked Genes; The Journal of Cell Biology, 111:1127–1135 (1990).

D. R. Greaves, et al.; Human CD2 3'-Flanking Sequen-

OTHER PUBLICATIONS ces Confer High-Level, T. Cell-Specific, Position-Independent Gene Expression in Transgenic Mice; Cell, 56:979-986 (1989).

J. M. Grichnik, et al.; Tissue restricted and stage specific transcription is maintained within 411 nucleotides flanking the 5' end of the chicken α-skeletal actin gene; Nucleic Acids Research, 14:1683-1701 (1986).

F. Grosveld, et al.; Position-Independent, High-Level Expression of the Human β-Globin Gene in Transgenic Mice; Cell, 51:975-985 (1987).

U. Gubler, et al.; Cloning and sequence analysis of cDNA for the precursor of human growth hormone-releasing factor, somatocrinin; Proc. Natl. Acad. Sci. USA, 80:4311-4314 (1983).

P. Gunning, et al.; Chromosomal location of the co-expressed human skeletal and cardiac actin genes; Proc. Natl. Acad. Sci. USA, 81:1813-1817 (1984).

P. Gunning, et al.; A human β-actin expression vector system directs high-level accumulation of antisense tanscripts; Proc. Natl. Acad. Sci. USA, 84:4831-4835 (1987).

P. Gunning, et al.; Isolation and Characterization of Full-Lenth cDNA Clones for Human α-, β-, and γ-Actin mRNAs: Skeletal but Not Cytoplasmic Actins Have an Amino-Terminal Cysteine that is Subsequently Removed; Molecular and Cellular Biology, 3:787-795 (1983).

P. L. Hallauer, et al.; Expression of a Quail Troponin I Gene in Transgenic Mice; Cellular and Molecular Biology of Muscle Development, p. 370, M425.

H. Hamada, et al.; Molecular structure and evolutionary origin of human cardiac muscle actin gene; Proc. Natl. Acad. Sci USA, 79:5901-5905 (1982).

K. E. M. Hastings, et al.; Generation of Troponin T Isoforms by Alternative RNA Splicing in Avian Skeletal Muscle, Conserved and Divergent Features in Birds and Mammals; The Journal of Biological Chemistry, 260:13699-13703 (1985).

D. M. Helfman, et al.; Isolation and Sequence of a cDNA Clone That Contains the Entire Coding Region for Chicken Smooth-muscle α-Tropomyosin; The Journal of Biological Chemistry; 259:14136-14143 (1984).

M. W. Hentze; Determinants and regulation of cytoplasmic mRNA stability in eukaryotic cells; Biochimica et Biophysica Acta, 1090:281-292 (1991).

M. Hoffman; Putting New Muscle Into Gene Therapy; Science, 254:1455-1456 (1991).

J. P. Hossle, et al.; The primary structure of chicken B-creatine kinase and evidence for heterogeneity of its mRNA; Nucleic Acids Research, 14:1449-1463 (1986).

C-Y. J. Hsu, et al.; Conserved and unique sequences in the 3'-untranslated region of rate smooth-muscle alpha-actin mRNA; Gene, 69:345-348 (1988).

M. C-T. Hu, et al.; The Complete Sequence of the Mouse Skeletal α-Actin Gene Reveals Several Conserved and Inverted Repeat Sequences Outside of the Protein-coding Region; Molecular and Cellular Biology, 6:15-25 (1986).

T. Jaenicke, et al.; The Complete Sequence of the Human β-Myosin Heavy Chain Gene and a Comparative Analysis of Its Product; Genomics, 8:194-206 (1990).

M. Jansen, et al.; Sequence of cDNA encoding human insulin-like growth factor I precursor; Nature, 306;609-611 (1983).

J-P. Jin, et al.; Isolation and Characterization of cDNA Clones Encoding Embryonic and Adult Isoforms of Rat Cardiac Troponin T; The Journal of Biological Chemistry, 264:14471-14477 (1989).

K. W. Jones; Muscle Cell Differentiation and the Prospects for Genetic Engineering; Br. Med. Bull., 36:173-180 (1980).

S. Kamada, et al.; Structure of 3'-downstream segment of the human smooth muscle (aortic-type) α-actin-encoding gene and isolation of the specific DNA probe; Gene, 84:455-462 (1989).

D. Katcoff, et al.; Construction and characterization of genomic DNA clones containing rat actin and myosin genes; Scientific Meetings is Israel, Israel Journal of Medical Sciences, 17:477 (1981).

P. Khandekar, et al.; Co-ordinate Control of Gene Expression, Muscle-specific 7 S RNA Contains Sequences Homologous to 3'-Untranslated Regions of Myosin Genes and Repetitive DNA; J. Mol. Biol. 180:417-435 (1984).

M. Kirby, et al.; Actin and Myosin Isoforms in Aneural and Malformed Chick Hearts, J. Mol Cell Cardiol, 22:955-964 (1990).

T. A. Kunkel; Rapid and efficient site-specific mutagenesis without phenotypic selection; Proc. Natl. Acad. Sci. USA, 82:488-492 (1985).

OTHER PUBLICATIONS

A. A. Lagrutta; Studies on the structure and expression of an avian myosin heavy chain gene; University Microfilms International Dissertation Information Service; Ann Arbor, Michigan (1992).

D. P. Leader, et al.; Isolation and Characterization of cDNA Clones from Mouse Skeletal Muscle Actin mRNA; DNA, 5:235–238 (1986).

T-C. Lee, et al.; Activation of Skeletal α-Actin Gene Transcription: The Cooperative Formation of Serum Response Factor-Binding Complexes over Positive cis-Acting Promoter Serum Response Elements Displaces a Negative-Acting Nuclear Factor Enriched in Replicating Myoblasts and Nonmyogenic Cells; Molecular and Cellular Biology, 11:5090–5100 (1991).

L. A. Leinwand, et al.; Isolation and characterization of human myosin heavy chain genes; Proc. Natl. Acad. Sci. USA, 80:3716–3720 (1983).

A. Lindahl, et al.; Cellular Aspects of Gene Therapy; Growth Factors in Health and Disease, Elsevier Science Publishers B.V. (1990).

C. M. Lloyd, et al.; Deletions of the 3' Untranslated and Flanking Regions of the γ-Actin Gene Can Alter Myoblast Morphology and Differentiation; Journal of Cellular Biochemistry, Alan R. Liss, Inc., New York, p. 220, B114 (1990).

J. C. Loyd, et al.; Isolation of a cDNA clone for the human muscle specific carbonic anhydrase, CAIII; Ann. Hum. Genet., 49:241–251 (1985).

P. Lomedico, et al.; The structure and evolution of the two nonallelic rat preproinsulin genes; Cell, 18:545–558 (1979).

J. Marie, et al.; Tissue-specific heterogeneity of the 3'-untranslated region of L-type pyruvate kinase mRNAs; Eur. J. Biochem, 158:33"(1986).

Y. Mayer, et al.; Expression of the genes coding for the skeletal muscle and cardiac actins in the heart; Nucleic Acids Research, 12:1087–1100 (1984).

J. D. McCully, et al.; Isolation and Characterization of a Previously Unrecognized Myosin Heavy Chain Gene Present in the Syrian Hamster; J. Mol. Biol. 218:657–665 (1991).

R. M. Meford, et al.; A Novel Mechanism of Alternative RNA Splicing for the Developmentlly Regulated Generation of Troponin T Isoforms from a Single Gene; Cell; 38:409–421 (1984).

R. M. Medford, et al.; Transcriptional and Cell Cycle-mediated Regulation of Myosin Heavy Chain Gene Expression during Muscle Cell Differentiation; The Journal of Biological Chemistry, 258:11063–11073 (1983).

D. Melloul, et al.; Developmentally regulated expression of chimeric genes containing muscle actin DNA sequences in transfected myogenic cells; The EMBO Journal, 3:983–990 (1984).

A. D. Miller, Progress Toward Human Gene Therapy; Blood, 76:271–278(1990).

P. P. Minghetti, et al.; Molecular Structure of the Chicken Vitamin D-Induced Calbindin-$D_{28K}$ Gene Reveals Eleven Exons, Six $Ca^{2+}$-Binding Domains, and Numerous Promoter Regulatory Elements; Molecular Endocrinology, 2:355–367 (1988).

A Minty, et al.; Muscle coding sequences and their regulation during myogenesis: cloning of muscle actin cDNA probes; Reprod. Nutr. Develop., 21:247–255 (1981).

A. J. Minty, et al.; Mouse Actin Messenger RNAs, Construction and Characterization of a Recombinant Plasmid Molecule Containing a Complementary DNA Transcript of Mouse α-Actin mRNA; The Journal of Biological Chemistry, 256:1008–1014 (1981).

A. Minty, et al.; Upstream Regions of the Human Cardiac Actin Gene That Modulate Its Transcription in Muscle Cell: Presence of an Evolutionarily Conserved Repeated Motif; Molecular and Cellular Biology, 6:2125–2136 (1986).

T. Miwa, et al.; Structure, Chromosome Location, and Expression of the Human Smooth Muscle (Enteric Type) γ-Actin Gene: Evolution of Six Human Actin Genes; Molecular and Cellular Biology, 11:3296–3306 (1991).

E. G. Nabel, et al.; Site-Specific Gene Expression in Vivo by Direct Gene Transfer into the Arterial Wall; Science, 249:1285–1288 (1990).

S-Y Ng, et al.; Evolution of the Functional Human β-Actin Gene and Its Multi-Pseudogene Family: Conservation of Noncoding Regions and Chromosomal Dispersion of Pseudogenes; Mol. Cell. Biol., 5:2720–2732 (1985).

B. Ni, et al.; Molecular cloning of calmodiulin mRNA species which are preferentially expressed in neurons in the rat brain; Molecular Brain Research, 13:7–17 (1992).

OTHER PUBLICATIONS

W. Nikovits, Jr., et al.; The chicken fast skeletal troponin I gene: exon organization and sequence; Nucleic Acids Research, 14:3377-3390 (1986).

U. Nudel, et al.; Isolation and Characterization of rat skeletal muscle and cytoplasmic actin genes; Proc. Natl. Acad. Sci. USA, 79:2763-2767 (1982).

C. P. Ordahl; Molecular cloning of Muscle-Regulated Gene Sets; Journal of Supramolecular Structure and Cellular Biochemistry, Alan R. Liss, Inc., New York; p. 411, 1104 (1981).

C. P. Ordahl, et al.; Strong homology in promoter and 3'-untranslated regions of chick and rat α-actin genes; Nature, 303:348-349 (1983).

K. Ozono, et al.; The Vitamin D-responsive Element in the Human Osteocalcin Gene; The Journal of Biological Chemistry, 265:21881-21888 (1990).

T. D. Palmer, et al.; Genetically modified skin fibroblasts persist long after transplantion but gradually inactivate introduced genes; Proc. Natl. Acad. Sci. USA, 88:1330-1334 (1991).

J. Parker-Thornburg, et al.; Structural and Developmental Analysis of Two Linked Myosin Heavy Chain Genes; Developmental Biology, 150:99-107 (1992).

M. S. Parmacek, et al.; Isolation of cDNA and Genomic Clones Encoding Murine Cardiac Troponin C and Expression of the Recombinant Protein in *E. Coli*; Clinical Research, 37:521A (1989).

M. L. Pearson; Introduction: Muscle Gene Structure and Expression; Muscle Development: Molecular and Cellular Control, Cold Spring Harbor Laboratory; Cold Spring Harbor, New York; pp. 55-60 (1982).

C. J. Petropoulos, et al.; The Chicken Skeletal Muscle α-Actin Promoter Is Tissue Specific in Transgenic Mice; Molecular and Cellular Biology 9:3785-3792 (1989).

P. Ponte, et al.; Evolutionary conservation in the untranslated regions of actin mRNAs: DNA sequence of a human beta-actin cDNA; Nucleic Acids Research; 12:1687-1696 (1984).

P. Ponte, et al.; Human Actin Genes Are Single Copy for α-Skeletal and α-Cardiac Actin but Multicopy for β- and γ-Cytoskeletal Genes: 3'0 Untranslated Regions Are Isotype Specific but Are Conserved in Evolution; Molecular and Cellular Biology, 3:1783-1791 (1983).

P. Ponte, et al.; mRNAs for the Single Copy Human Sarcomeric α- and Cardiac-Actin Genes, and for the Multiple copy Cytoskeletal γ- and γ-Actin Genes: 3' Untranslated Regions are Nonhomologous but are Conserved in Evolution, American Society of Biological Chemists, San Francisco, California, 2100 (1983).

Zhu, Y-Y, et al., "Phorbol esters Selectively Down-regulate Contractile Protein Gene Expression in Terminally Differentiated Myotubes Through Transcriptional Repression and Message Destabilization" *J. Cell Biology* 115:745-754 (1991).

J. P. Rao, et al.; Transcriptional activity at the 3' end of the actin gene at 5C on the X chromosome of *Drosophia melanogaster*; Biochimic et Biophysica Acta 950:30-44 (1988).

S. Reddy, et al.; Structure of the Human Smooth Muscle α-Actin Gene; The Journal of Biological Chemistry, 265:1683-1687 (1990).

M. J. Renan; Conserved Elements in the 3' Untranslated Regions of c-fos and Actin mRNAs Bioscience Reports, 6:819-825 (1986).

H. E. Richter, et al.; Screening of a Bovine Genomic Library for Myosin Heavy-Chain Genes; J. Anim. Sci., 64:607-614 (1987).

J. Robbins, et al.; Isolation of Multiple Genomic Sequences Coding for Chicken Myosin Heavy Chain Protein; The Journal of Biological Chemistry, 257:549-556 (1982).

M. Rotter, et al.; The human embryonic myosin alkali light chain gene: use of alternative promoters and 3' non-coding regions; Nucleic Acids Research, 19:1497-1504 (1991).

D. Rudman, et al.; Effects of Human Growth Hormone in Men Over 60 Years Old; The New England Journal of Medicine, 323:1-6 (1990).

L. Saez, et al.; Characterization of diverse forms of myosin heavy chain expressed in adult human skeletal muscle; Nucleic Acids Reseach, 14:2951-2969 (1986).

C. Saidapet, et al.; Tissue Specificity of 3'-Untranslated Sequence of Myosin Light Chain Gene: Unexpected Interspecies Homology with Repetitive DNA; Archives of Biochemistry and Biophysics, 233:565-572 (1984).

D. St. Louis, et al.; An alternative approach to somatic cell gene therapy; Proc. Natl. Acad. Sci. USA, 85:3150-3154 (1988).

K. Sato, et al.; Stability of CAT gene transcript depends

OTHER PUBLICATIONS on the 3'-end structure; Nucleic Acids Research, Symposium Series No. 21, 23-24 (1989).

R. Scharfmann, et al.; Long-term in vivo expression of retrovirus-mediated gene transfer in mouse fibroblast implants; Proc. Natl. Acad. Sci. USA, 88:4626-4630 (1991).

R. F. Selden, et al.; Implantation of Genetrically Engineered Fibroblasts into Mice: Implications for Gene Therapy; Science, 236:714-718 (1987).

M. Shaffer; Genetically altered muscle cells prove useful in hemophilia B; Biotechnology Newswatch, p. 12 (1992).

M. Shani, et al.; Skeletal muscle actin mRNA. Characterization of the 3' untranslated region; Nucleic Acids Research; 9:579-589 (1981).

P. M. Sharma, et al.; Cloning and expression of a human muscle phosphofructokinase cDNA; Gene, 77:177-183 (1989).

D. R. Shaw, et al.; The 3'-Noncoding Region of the Chick Myosin Light-Chain Gene Hybridizes to a Family of Repetitive Sequences in the Slime Mold *Dictyostelium discoideum;* Archives of Biochemistry and Biophysics, 246:829-837 (1986).

A. Sidya, et al; Characterization of Six Biology, 5:3168-3182 (1985). Chicken Genomic Clones Coding For Myosin Heavy Chain Carboxyl Terminus And Noncoding Region; FASEB J. 2(4):545 (1988).

R. H. Singer, et al.; Messenger RNA in HeLa Cell: Kinetics of Formation and Decay; J. Mol. Biol., 78:321-334 (1973).

H. Stedman, et al.; Molecular Genetics in Basic Myology: A Rapidly Evolving Perspective; Muscle & Nerve, 11:668-682 (1988).

E. E. Strehler, et al.; Myosin Light-Chain 1 and 3 Gene Has Two Structurally Distinct and Differentially Regulated Promoters Evolving at Different Rates; Molecular and Cellular Biology, 5:3168-3182 (1985).

J. Teumer, et al.; Human growth hormone in the blood of athymic mice grafted with cultures of hormone-secreting human keratinocytes; The FASEB Journal, 4:3245-3250 (1990).

K. Tokunaga, et al.; Isolation of cDNA Clones for Mouse Cytoskeletal γ-Actin and Differential Expression of Cytoskeletal Actin mRNAs in Mouse Cells; Molecular and Cellular Biology, 8:3929-3933 (1988).

S. E. Tollefsen, et al.; Insulin-like Growth Factors (IGF) in Muscle Development; The Journal of Biological Chemistry, 264:13810-13817 (1989).

J. A. Wolff, et al.; Conditions Affecting Direct Gene Transfer into Rodent Muscle *In Vivo;* BioTechniques, 11:474-485 (1991).

J. A. Wolff, et al.; Direct Gene Transfer Into Mouse Muscle In Vivo; Journal of Cellular Biochemistry, Wiley-Liss, p. 376, D434 (1990).

J. A. Wolff, et al.; Direct Gene Transfer into Mouse Muscle in Vivo; Science, 247:1465-1468 (1990).

D. Yaffe, et al.; Highly conserved sequences in the 3' untranslated region of mRNAs coding for homologous proteins in distantly related species; Nucleic Acids Research, 13:3723-3737 (1985).

R. Zakut, et al.; Nucleotide sequence of the rat skeletal muscle actin gene; Nature, 298:857-859 (1982).

M. J. Zoller, et al.; Oligonucleotide-Directed Mutagenesis of DNA Fragments Cloned into M13 Vectors; Methods in Enzymology, 100:468-500 (1983).

Lee, Te-Chung, et al., "Displacement of BrdUrd-induced YY1 by serum response factor activates skeletal α-actin transcription in embryonic myoblasts" *Proc. Natl. Acad. Sci.* USA 89:9814-9818 (1992).

Lee, Te-Chung, et al., "Activation of Skeletal α-Actin Gene Transcription: The Cooperative Formation of Serum Response Factor-Binding Complexes over Positive cis-Acting Promoter Serum Response Elements Displaces a Negative-Acting Nuclear Factor Enriched in Replicating Myoblasts and Nonmyogenic Cells *Molecular and Cellular Biology* 11:5090-5100 (1991).

Kaneda, Y., et al., "Increased Expression of DNA Cointroduced with Nuclear Protein in Adult Rat Liver"-*Science* 243:375-378 (1989).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 275 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
TAAACATGTT  TACATGATCA  CTTTGCCAAC  CACACTCAGG  ATGACAATCT  TGTAGGTTCC    60

AGGCTGCTGA  GGACCTGCAC  CAGCCATGCA  ACTTTCTATT  TTGTAACAAT  TTCTGGTTAC   120

TGTTGCTGCA  AAGCCCATGT  GACACAGTGT  ATGTAAAGTG  TACATAAATT  AATTTATTTT   180

ACCTCGTTTT  GTTTGTTTTT  AAAACCAATG  CCCTGTGGAA  GGAAACATAA  AACTTCAAGA   240
```

AGCATTAAAT CATCAGTCAT TCTGTCACAC CCCTA  275

(2) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGTGACTCAC CGGGTGAACG GGGCATT  27

MYOGENIC VECTOR SYSTEMS

This invention was partially supported by a grant from the United States government under HL-38401 awarded by the National Institute of Health. The Government has certain rights in the invention.

FIELD OF THE INVENTION

The present invention relates generally to expression vectors for use in expressing polypeptides in myogenic cells. More particularly it relates to vectors containing the skeletal alpha actin gene promoter and the corresponding 3' transcribed but untranslated region of the gene and the contiguous noncoding DNA containing the gene's natural transcriptional termination region.

BACKGROUND OF THE INVENTION

Actin is a contractile protein found in most cell types. Actin proteins are represented by similar but nonidentical isoforms which in warm blooded vertebrates are encoded by multigene families. Actin is expressed in a developmentally timed dependent and tissue specific manner, in which adult muscle tissues express exclusively the skeletal alpha actin gene as the predominant actin isoform. The nucleic acid sequence of skeletal alpha actin gene has been characterized in chicken, rat, mouse and human. Fornwald et al., Nucleic Acids Res., Vol. 10, pp. 3861-3876 (1982); French et al., Gene, Vol. 88, pp. 173-180 (1990); Zak et al., Nature, Vol. 298, pp. 857-859 (1982); Hu et al., Mol. Cell. Biol., Vol. 6, pp. 15-25 (1986) and Minty and Kedes, Mol. Cell. Biol., Vol. 6, pp. 2125-2136 (1986).

Once a gene has been characterized and sequenced it can be mapped to determine its protein coding and noncoding portions. RNA transcripts are initiated from a promoter region start site at the messenger RNA cap and continue through the protein coding region to the noncoding region involved with transcriptional termination. Post transcriptional processing of the RNA transcripts removes the noncoding introns to form a continuous coding sequence. Further, there is progressive trimming of the RNA transcript to the polyadenylation signals, found in the noncoding 3' untranslated portion of the processed messenger RNA. The levels of messenger RNA biosynthesis and accumulation is determined by parts of the unexpressed portion of the gene. For example the promoter, which is part of the unexpressed portion of the gene, is involved in determining gene expression. It regulates when and how the expressed gene is transcribed. The accumulation of RNA transcripts, however, may relate to the intrinsic stability of that RNA in a particular cell type. This intrinsic stability is dependent on sequences within the MRNA that provide stabilization. Thus, the ability to express a particular gene product is a balance between transcription rate and the stability of the MRNA transcript.

Expression of the actin gene family is tissue specific. The skeletal alpha actin protein is expressed primarily in cardiac and skeletal muscle tissues. Transient transfection experiments indicated that regions within the 200 bp promoter region are sufficient for tissue restricted expression in primary myoblasts. Bergsma, et al, Mol. Cell. Biol., Vol.6 pp. 2462-2475 (1986) and Chow and Schwartz Mol. Cell Biol., Vol.10 pp. 528-538 (1990). Further, the promoter region harbors conserved cis-acting elements to accurately initiate skeletal alpha actin transcripts from the bacterial reporter gene chloramphenicol acetyltransferase (CAT) in differentiating myoblasts. Grichnik et al. Nucleic Acids Res., Vol. 14, pp. 1683-1701 (1986). Transgenic mice with an integrated skeletal alpha actin promoter showed preferential expression of the CAT gene in myogenic tissues Petropulous et al. Mol. Cell. Biol., Vol. 9 pp. 3785-3792 (1989). It is also known that CAT activity is detectable as early as 10 days in the mouse embryo when the embryonic heart is first being formed. Further, CAT activity can be induced in newborn skeletal muscle. Thus, the skeletal actin promoter can switch transcriptional activity in mammalian systems, to provide muscle restricted expression. However, when measurements were made to compare the levels of CAT messenger RNA to that of the endogenous skeletal alpha actin messenger RNA (which in the adult muscle was found at levels over thousand fold higher than the embryo), the CAT messenger RNA could not be detected by standard RNA blotting techniques. These experimental results showed that even though small amounts CAT protein accumulated in skeletal muscle, the CAT messenger RNA never accumulated to the levels of RNA transcripts from the endogenous skeletal actin gene.

Current trends for optimizing gene transcription vectors have been directed towards increasing the transcriptional activity of the vector system. For example, Observations in the human Beta globin gene system indicated that expression in transgenic mice was never as high as the expression of the endogenous mouse Beta globin gene. Grosveld and co-workers Cell, Vol. 51, pp 975-985 (1987) It was determined that the sites surrounding the globin locus contain a number of DNAse hypersensitive sites that are termed the dominant control region. This region appears to act as tissue specific enhancers. When some of these sites were cloned into a minilocus gene it provided erythroid tissue specific expression in transgenic animals. Regulatory sequences similar to the dominant control regions have been described for human CD2. Greaves et al. Cell, Vol. 56, pp. 979-986 (1988). It is known that the avian skeletal actin promoter is as active as the SV40 promoter which is a standard for high levels of expression. Bergsma, et al, (1986). Hence, the skeletal actin promoter is not the cause for low levels of messenger RNA accumulation. Thus, the actin promoter is by itself insufficient to drive the expression of other gene products to accumulate at levels which are comparable to the intact skeletal alpha actin MRNA.

The rate of metabolic breakdown of MRNA molecules is an important factor in the regulation of gene expression. The rates of decay of individual MRNA species can affect strongly the steady state levels of these species in the cytoplasm. Consequently, the extent of expression of a given gene, as measured by the rate of synthesis of the corresponding protein, will be dependent to a large extent on the degree of stability of the MRNA derived from this gene. Messenger RNA from skeletal muscle was previously shown to be distributed into two populations with regard to its stability. Medford et al. J. Biol. Chem., Vol. 258, pp. 11063-11073 (1983). One MRNA population had a half life of less than 4 hours and the other population had a half-life of 17-to over 54 hours.

Comparison of the untranslated regions in vertebrate skeletal alpha, cardiac alpha, and beta actin MRNA has revealed regions of high sequence homology within the 3' untranslated portion of each of these actin isoformic MRNA and that this homology is greater among the alpha-cardiac and skeletal actin isoforms than between alpha striated actin and beta actin isoform MRNA. Mayer et al., Nucl. Acids Res., Vol 12. pp. 1087-1100 (1984); Ponte et al., Nucl. Acids Res., Vol. 12 pp. 1687-1696 (1984); Chang et al., Nucl. Acids Res., Vol. 13 pp. 1223-1237 (1985). In comparison, other vertebrate genes, such as those encoding insulin and prolactin share common coding regions but usually contain divergent 3' untranslated regions. The preservation of the 3' untranslated regions of the skeletal alpha actin gene in animal species ranging from birds to humans suggests that they have important biological roles. In the present invention, the incorporation of the myogenic specifies 3' untranslated region into recombinant DNA vectors for expressing polypeptides in muscle tissue was found to be highly advantageous, since it enhanced the polypeptide MRNA content in muscle by increasing stability.

SUMMARY OF THE INVENTION

An object of the present invention is a myogenic vector system capable of expressing any specific nucleic acid sequence in myogenic tissue.

An additional object of the present invention is a regulatable myogenic vector system.

A further object of the present invention is a method for treating muscle atrophy in aging humans.

Another method of the present invention is a method for treating muscle atrophy induced by spinal cord injuries or muscular disease.

A further object of the present invention is a method of preventing or treating atherosclerotic cardiovascular disease.

An additional method of the present invention is the introduction of a myogenic vector system for gene replacement.

A further object of the invention is a method for vaccine production in human or animals.

Another object of the present invention is a method of treating growth disorders.

Thus, in accomplishing the foregoing objects, there is provided in accordance with one aspect of the present invention a myogenic vector system (ANS) for the expression of a nucleic acid sequence in myogenic tissue comprising a promoter; a cassette whose 5' end is attached to the 3' end of the promoter, the cassette containing a nucleic acid sequence which is to be expressed; a myogenic specific 3' untranslated region (3' UTR) and a non-coding region (NCR) contiguous to the 3' end of the 3' UTR, the NCR containing a transcriptional termination signal, wherein the 5' end of the 3' UTR is attached to the 3' end of the cassette.

Specific embodiments of the MVS of the present invention can further include a leader sequence following the promoter region. Additional embodiments of the MVS include a first intron, an initiation ATG and NcoI cloning site inserted between the promoter leader region area and the cassette area. Specific embodiments of the cassette include an EcoR1 site at the 3' end. The 3' UTR can have an EcoRV site at its 5' end.

Any promoter will work although in the preferred embodiment a myogenic promoter selected from a group consisting of skeletal alpha actin gene promoter, first myosin light chain 1 promoter, myosin heavy chain promoter, tropinin T promoter, muscle creatinine kinase promoter/enhancer, cytomegalovirus promoter, RSV promoter and Rous Sarcoma virus LTR. In the preferred embodiment the skeletal alpha actin promoter is used.

Similarly, the 3' UTR and NCR are selected from any myogenic specific genes. In the preferred embodiment the skeletal alpha actin gene 3' UTR and NCR regions are used.

Specific embodiment also include the addition of regulatory promoter elements to regulate the expression of any specific nucleic acid sequence in myogenic tissue. In the preferred embodiment, Vitamin D is used to regulate expression.

The cassette can contain any of a variety of nucleic acid sequences which expressed a polypeptide. This can include hormones, growth factors, enzymes, apolipoprotein, clotting factors, AIDS viral coat proteins, viral component proteins, viral surface proteins, bacterial surface proteins, parasitic cell surface proteins, tumor suppressors and viral reverse transcriptase.

For specific embodiments the cassette contains the nucleic acid sequence for the insulin like growth factor 1, insulin like growth factor II, insulin growth factor binding protein, growth hormone releasing factor, apolipoprotein A-1 or a protein capable of inducing an antibody response.

The MVS is used to treat muscle atrophy in aging humans, muscle atrophy induced by spinal cord injuries or neuromuscular diseases, amyotrophic lateral sclerosis and growth disease. It is also useful in the treatment of prevention of atheroselerotic cardiovascular disease, gene replacement, and vaccine production.

Other and further objects features and advantages will be apparent from the following description of the presently preferred embodiments of the invention, which are given for the purpose of disclosure, when taken in conjunction with the accompanying drawings.

Figure 1:
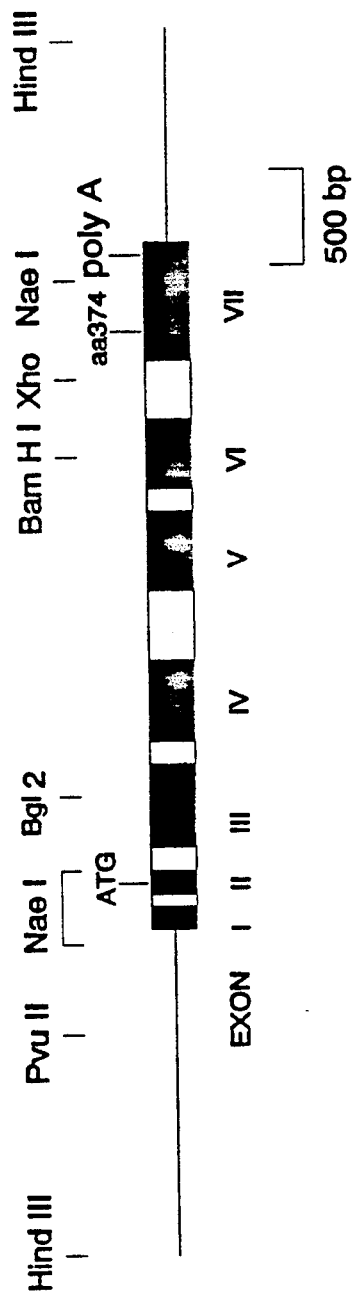
FIG. 1 is a schematic drawing of the chicken skeletal alpha actin gene which includes location of unique restriction sites.

The drawings are not necessarily at this scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

The term "promoter" as used herein refers to a recognition site on a DNA strand to which the RNA polymerase binds. The promoter usually is a DNA fragment of about 100 to 200 bp in the 5' flanking DNA upstream of the cap site or the transcriptional initiation start site. The promoter forms an initiation complex with RNA polymerase to initiate and drive transcriptional activity. The complex can be modified by activating sequences termed "enhancers" or inhibiting sequences termed "silencers." Usually specific regulatory sequences or elements are embedded adjacent to or within the protein coding regions of DNA. The elements, located adjacent to the gene, are termed cis-acting elements. These signals are recognized by other diffusible biomolecules in trans to potentiate the transcriptional activity. These biomolecules are termed transacting factors. The presence of transacting factors and cis-acting elements have been shown to contribute to the timing and developmental expression pattern of a gene. Cis acting elements are usually thought of as those that regulate transcription and are found within promoter regions and other upstream DNA flanking sequences.

The term "leader" as used herein refers to a DNA sequence at the 5' end of a structural gene which is transcribed along with the gene. The leader usually results in the protein having an N-terminal peptide extension sometimes called a pro-sequence. For proteins destined for either secretion to the extracellular medium or a membrane, this signal sequence, which is largely hydrophobic, directs the protein into endoplasmic reticulum from which it is discharged to the appropriate destination.

The term "intron" as used herein refers to a section of DNA occurring in the middle of a gene which does not code for an amino acid in the gene product. The precursor RNA of the intron is excised and is therefore not transcribed into MRNA nor translated into protein.

The term "cassette" refers to the sequence of the present invention which contains the nucleic acid sequence which is to be expressed. The cassette is similar in concept to a cassette tape. Each cassette will have its own sequence. Thus by interchanging the cassette the vector will express a different sequence. Because of the restrictions sites at the 5' and 3' ends, the cassette can be easily inserted, removed or replaced with another cassette.

The term "3' untranslated region" or "3' UTR" refers to the sequence at the 3' end of a structural gene which is usually transcribed with the gene. This 3' UTR region usually contains the poly A sequence. Although the 3' UTR is transcribed from the DNA it is excised before translation into the protein. In the present invention it is preferred to have a myogenic specific 3' UTR. This allows for specific stability in the myogenic tissues.

The term "Non-Coding Region" or "NCR" refers to the region which is contiguous to the 3' UTR region of the structural gene. The NCR region contains a transcriptional termination signal.

The 3' UTR and NCR are a key aspect of the present invention because they provide a higher level of MRNA accumulation through increased MRNA stability in myogenic cells rather than non-myogenic cells. Thus, this increased stability of MRNA leads to the increased levels of protein production.

The 3' untranslated region of the chicken skeletal alpha actin gene which starts at nucleotide 2060 and extends to 2331. The complete 3' untranslated region and contiguous noncoding DNA extends an additional 2.0 Kb. This 2.3 Kb fragment can be linked immediately following the natural translation termination codon to a copy DNA sequence coding for a polypeptide desired to be expressed.

The term "myogenic" or "myogenic specific" refers to muscle tissue. The muscle tissue can be in vivo tissue, in vitro tissue or in vitro tissue cultures of cells capable of differentiating into muscle tissue. Myogenic cells include skeletal, heart and smooth muscle cells. These vectors are transfected into myogenic cells in culture, and are injected into intact muscle tissue. These vectors containing the construction are injected into mammalian oocytes and may be stably incorporated into the genome to generate transgenic animals, in which the vector expresses polypeptides in myogenic cells.

The term "restriction site" refers to a sequence specific cleavage site of restriction endonucleases.

The term "vector" refers to some means by which DNA fragments can be introduced into a host organism or host tissue. There are various types of vectors including plasmid, bacteriophages and cosmids.

The term "effective amount" means sufficient NWS is injected into myogenic tissue or culture to produce the adequate levels of the polypeptide. One skilled in the art recognizes that this actual level will depend on the use of the MVS. The levels will be different in treatment, vaccine production, or vaccination.

In one embodiment of the present invention there is a myogenic vector system (MVS) for the expression of a nucleic acid sequence in myogenic tissue, comprising a promoter; a cassette whose 5' end is attached to the 3' end of the promoter; a myogenic specific 3' UTR and a NCR contiguous to the 3' end of the 3' UTR.

This basic system can be enhanced in a variety of ways including the addition of a leader sequence between the promoter and cassette.

In a preferred embodiment the MVS for expression of a nucleic acid sequence in myogenic tissue comprises a functional unit which expresses the nucleic acid sequence. The functional unit is comprised of elements all sequentially linked together 5' to 3'. The elements in the order of linkage include a promoter, a 5' MRNA leader sequence, a first intron and initiation ATG and NcoI cloning site, a cassette which has a EcoRI site at its 3' end, a myogenic specific 3' UTR in which the 5' end of the 3' UTR has an EcoRV site, and a NCR which is contiguous to the 3' end of the 3' UTR.

A variety of promoters can be used in the MVS. Some examples include skeletal alpha actin gene promoter, first myosin light chain 1 promoter, myosin heavy chain promoter, tropinin T promoter, muscle creatinine kinase promoter, cytomegalovirus promoter, RSV promoter and Rous Sarcoma virus LTR. In the preferred embodiment, a myogenic specific promoter such as the skeletal alpha actin gene promoter is used.

The 3' UTR and NCR can be selected from any group of myogenic specific genes. Examples of genes in this group are the skeletal alpha actin gene, fast myosin light chain 1 gene, myosin heavy chain gene, tropinin T gene, acetyl choline receptor subunit genes and muscle creatinine kinase gene. In the preferred embodiment, the 3' UTR and NCR are from the skeletal alpha actin gene.

Alternate embodiments of the present invention include the addition of a regulator system for regulating the expression of nucleic acid sequence.

Any of a variety of regulator systems can be used. In the preferred embodiment, two different regulatory systems have been used.

One embodiment of a regulated MVS (see FIG. 7) for the expression of a specific nucleic acid sequence in myogenic tissue, is comprised of a first functional unit and a second functional unit. The first functional unit and second functional unit can be in the same vector or in two separate vectors. In either case both functional units must be introduced into the myogenic tissue.

The first functional unit is composed of the following elements all sequentially linked 5' to 3': a myogenic specific promoter, a nucleic acid sequence coding for a receptor, a myogenic specific 3' UTR and a myogenic specific NCR.

The second functional unit is composed of the following elements sequentially linked 5' to 3': a response element corresponding to the receptor, a thymidine kinase promoter, a cassette containing the specific nucleic acid sequence of interest, a myogenic specific 3' UTR and a contiguous myogenic specific NCR.

In this regulatable MVS, it is preferable for the first functional unit to continuously express the receptor. It is preferable to use a receptor which is not found in high levels in myogenic tissue, when the agent which is specific to the receptor is introduced into the system. The receptor forms an interaction with the response element and the specific agent. This binding interaction causes the thymidine kinase promoter to express the specific nucleic acid sequence. By regulating the amount of agent which is present, The activity of the MVS is regulated.

In this regulatable system, the response element and receptor are usually complimentary and can be selected from a variety of receptor groups. For example, any vitamin, steroid, thyroid, orphan, hormone, retinoic acid and thyroxine can be used. In the preferred embodiment, the Vitamin D receptor and Vitamin D response element are used. In this case, ingestion of Vitamin D, for instance by drinking milk, raises the level of Vitamin D in the blood. This binds to the receptor being generated in the myogenic tissue and the complex binds to the receptor element causing the expression of the gene of interest. Thus, the MVS can be regulated by dietary intake.

Figure 9:
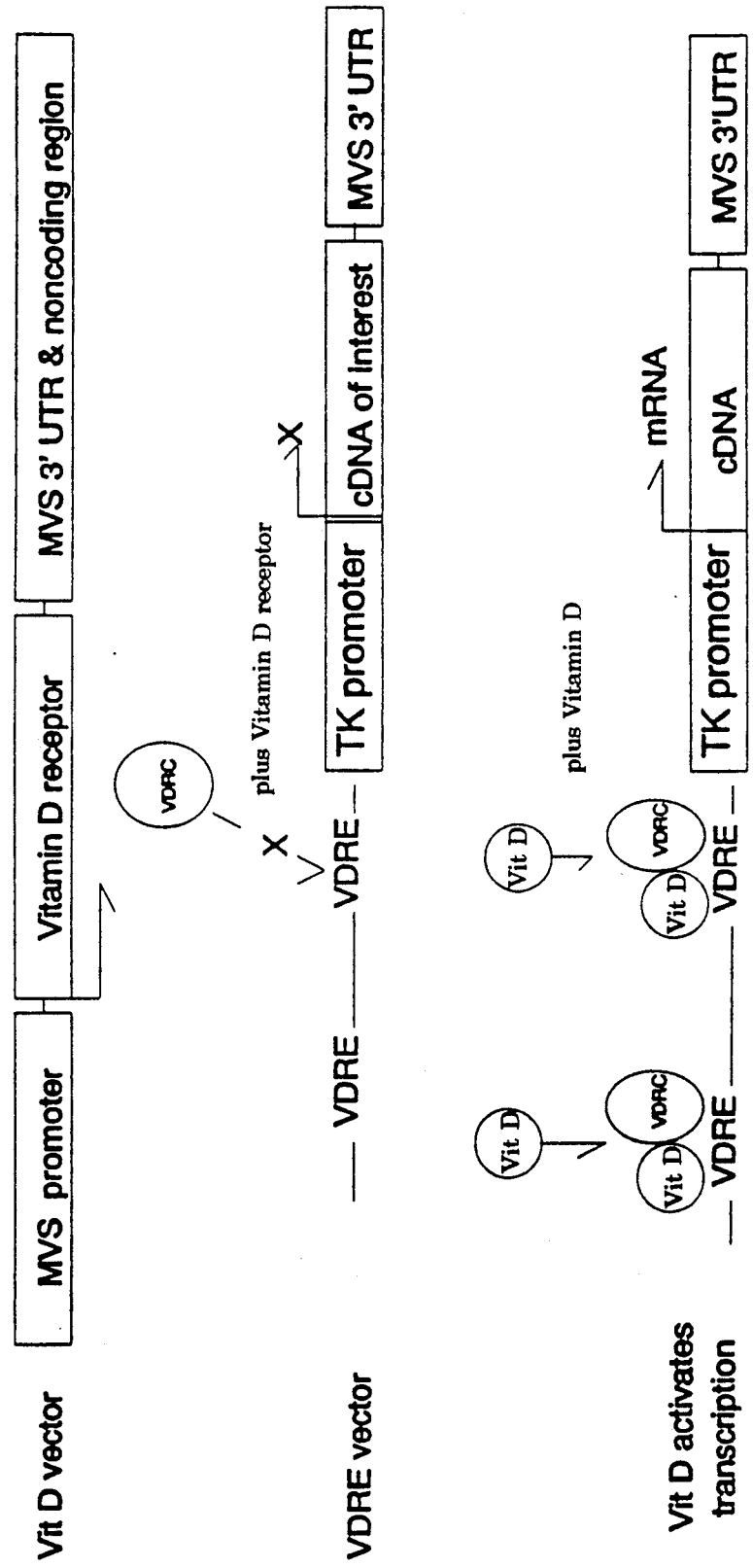
FIG. 9 is a schematic representative of a regulatable MVS using a chimeric receptor.

An alternate method of regulating the MVS is shown in FIG. 9. In this embodiment, at least one of the serum response elements in the alpha actin promoter region is made into a receptor binding site. Then a chimeric transfactor is constructed in which the normal DNA binding domain of the serum response factor is replaced with the DNA binding domain of the receptor. The transactivation domain of the serum response factor is not changed. Thus, when an agent or ligand specific to the receptor is present it binds to the receptor in the binding domain allowing the serum response transactivation factor to activate transcription. Thus, the regulation can be controlled by controlling the amount of the agent. The DNA binding domain which is substituted into the normal serum response factor is usually selected from the following families of receptors binding domains: the vitamin, steroid, thyroid, orphan, hormone, retinoic acid and thyroxine. In the preferred embodiment, the Vitamin D receptor is used.

The cassette can contain the nucleic acid sequence of interest and include any nucleic acid sequence which is to be expresses in the myogenic tissue or tissue culture. These nucleic acid sequence can call for any variety of polypeptides. The polypeptide can be any desired polypeptide including but not limited to known proteins. For example, the sequence could code for a hormone, a growth factor, an enzyme, an apolipoprotein, tumor suppressor, tumor antigen, a viral protein, a clotting factor and any proteins associated with the AIDS virus, any other viral proteins, including viral surface coat proteins, bacterial surface proteins, parasitic cell surface proteins, viral reverse transcriptase and any gene which needs to be replaced by gene replacement.

In specific embodiments of the MVS, the cassette included the nucleic acid for the insulin like growth factor I, or the insulin like factor II or the insulin growth binding protein. This specific embodiment can be used to treat muscle atrophy in aging humans, muscle atrophy induced by spinal cord injuries or neuromuscular diseases. A specific example of the latter case would be amyotrophic lateral sclerosis.

Another specific embodiment is a MVS where the cassette contains the nucleic acid sequence coding for growth hormone releasing factor. This MVS can be used for treating muscle atrophy in aging humans.

Another embodiment of the present invention includes an MVS where the cassette includes the nucleic acid sequence for apolipoprotein A-I. This MVS can be used for prevention or treatment of atherosclerotic cardiovascular disease.

In those instances where the MVS cassette contains a sequence coding for a viral, bacterial or parasitic protein, the MVS can be used to make a vaccine. In this the procedure for making a vaccine humans or animals, comprising the step of injecting an effective amount of the MVS into skeletal muscle or into tissue culture. In this MVS vector the cassette contains a nucleic acid sequence which codes for a polypeptides capable of eliciting an antibody response. This procedure would be a safe and effective method for generating vaccines. The vaccine can be generated in tissue culture, or in vivo in humans or animals. Examples of nucleic acid sequences which can elicit an antibody response include those for the viral proteins, bacterial proteins, and parasitic proteins. A specific case example is the AIDS proteins.

Another specific embodiment of the present invention is a method of treating growth disease which comprises the step of injecting an effective amount of an MVS into skeletal muscle wherein the nucleic acid sequence in the cassette contains the growth hormone sequence.

Another application of the present invention is a method for gene replacement. In this embodiment, an effective amount of the MVS is injected into skeletal muscle and the cassette contains any sequence which codes for a defective gene. For example, the genes for glycogen phosphorylase, alpha-1-antitrypsin and dystrophin can be inserted into the cassette. Individuals with the corresponding diseases of glycogen storage disease, alpha-1-antitrypsin deficiency or pulmonary emphysemia and Duchenne's Muscular Dystrophy would thus produce a sufficient amount of the normal polypeptide. The expressed protein may systemically spread throughout the animal via the circulatory blood system as well as remain in the injected musculature. The polypeptide may be harvested and purified as desired.

Any of the MVS's discussed herein can be further modified to enhance uptake by the cell. This enhancement comprises adding a coating. The coating includes a DNA initiation complex and histones. The initiation complex comprises a serum response factor (SRF), a transcription initiation factor (TIF) and a transregulatory factor (TRF). The SRF is attached to the serum response element within the promoter region of the MVS. The TIF and the TRF then interact with the SRF and the TATA box within the promoter to form a stable DNA complex. The histones bind nonspecifically to the remaining DNA in the MVS.

The following examples are offered by way of illustration and are not intended to limit the invention in any manner.

EXAMPLE 1

Isolation of the Chicken Skeletal Alpha Actin Gene

Figure 2:
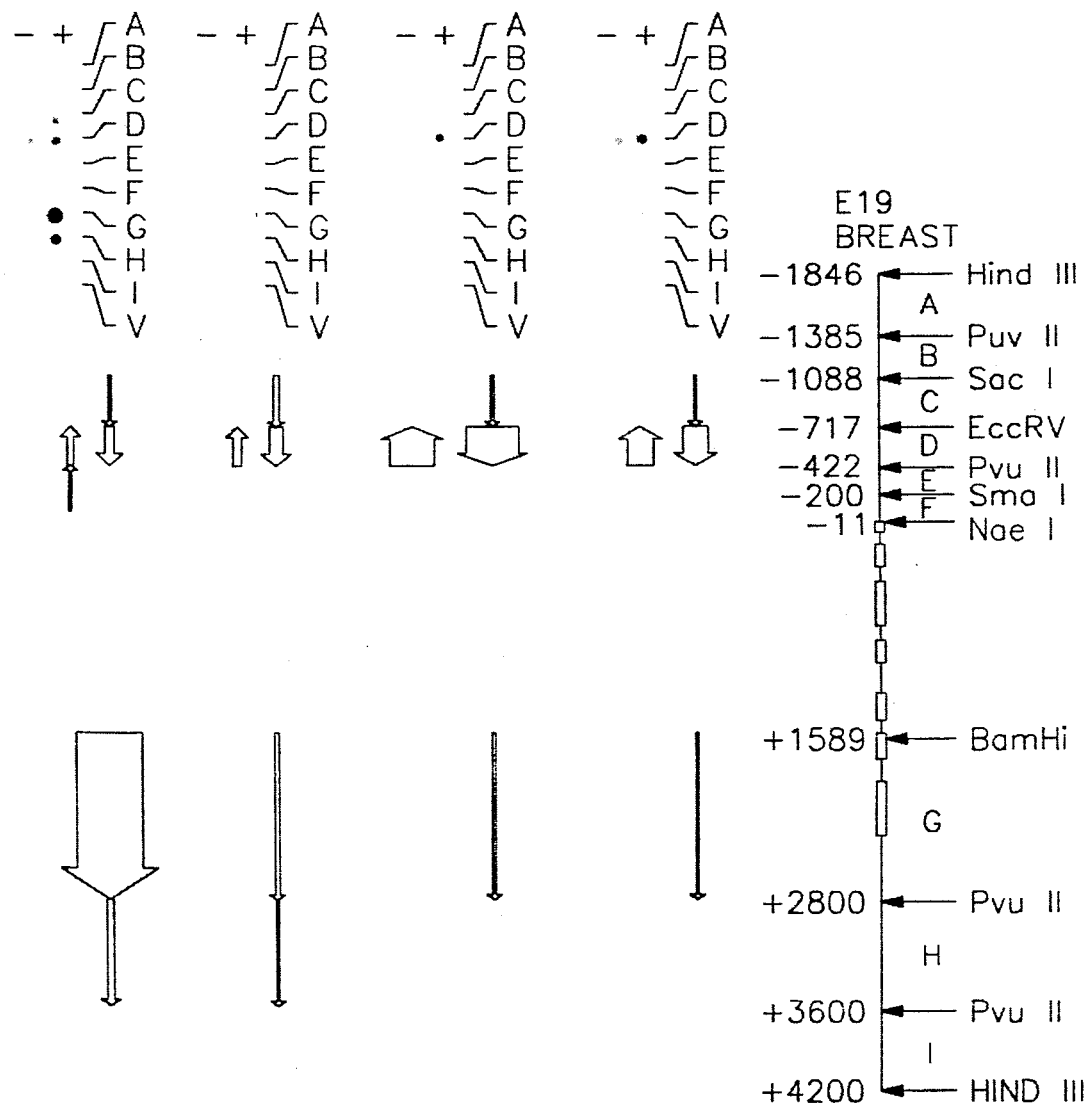
FIG. 2 illustrates the transcriptional domain of the avian skeletal alpha actin gene and the contiguous non-coding region where transcription terminates.

The 25 Kb EcoR1 fragment of chicken genomic DNA isolated from a lambda Charon 4A vector, contains the 6.2 Kb skeletal alpha actin gene on a single Hind III site of pBR322 is shown in FIG. 1. Chang et al. Mol. Cell. Biol. Vol 4:2498–2508 (1984). Nuclear transcription runoffs were used to map the transcriptional domain of the skeletal alpha actin gene (FIG. 2). DNA probes which encompassed portions of the 5' noncoding, promoter, coding, and the contiguous 3' noncoding regions were cloned into M13 vectors which provided sense and antisense probes. Nuclei isolated from fibroblasts, myoblasts and day 19 embryonic muscle cells were used in in vitro transcription assays to extend RNA transcripts with radioactive tagged nucleotides. Labeled RNA hybridized to dotted DNA probes showed that transcription terminates approximately 1 kb downstream of the skeletal alpha actin gene's poly A addition site. This is within a 800 bp Pvu II fragment between +2800 and +3600 nucleotides from the start of transcription.

Figure 3:
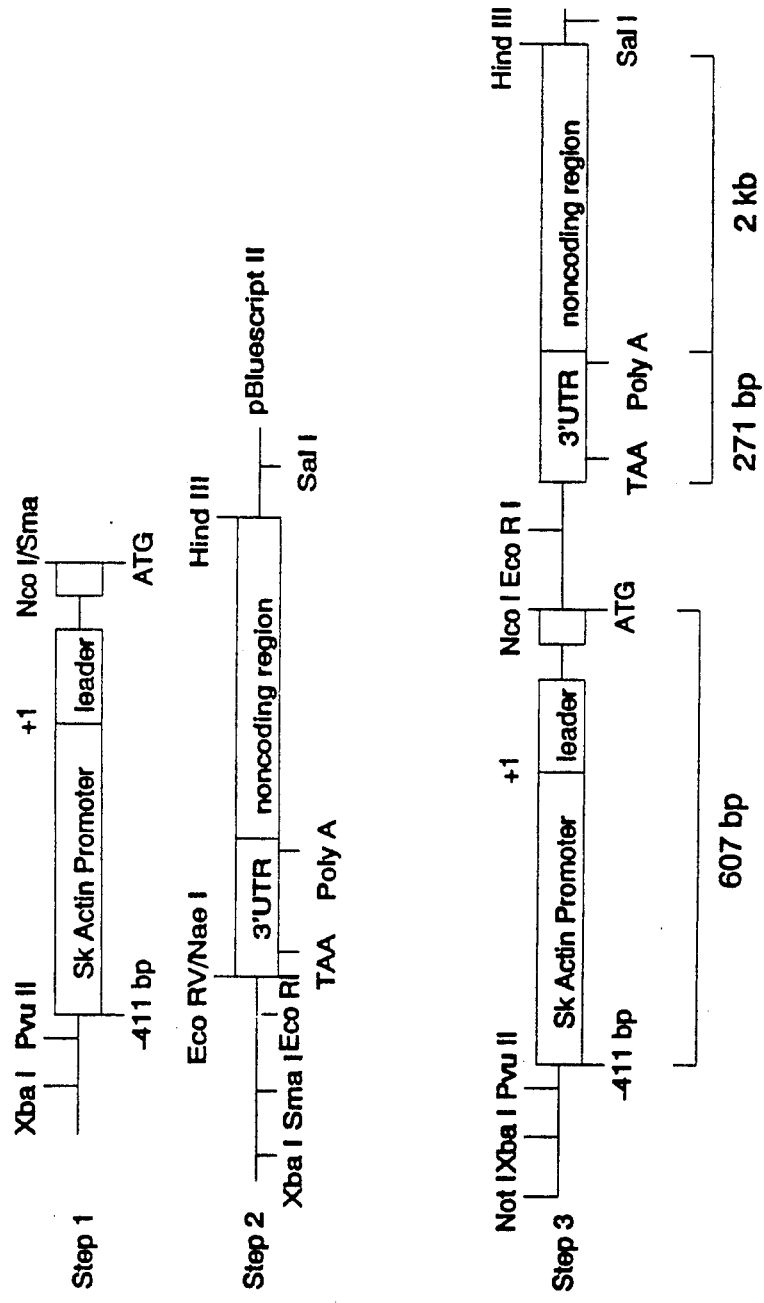
FIG. 3 is a schematic representation of a myogenic vector system.

The 3' untranslated region (3' UTR) and the contiguous noncoding region (NCR) can be isolated by restriction endonucleases digestion of the 6.2 Kb actin gene with blunt cutter Nae I, which cuts 30 bp upstream of the translation termination codon TAA. Hind III releases the 3' most portion of the actin gene from the vector pBR322 (FIG. 3). The 3' UTR and NCR were used to prepare DNA constructs. The skeletal alpha actin promoter and DNA flanking sequences (at least 411 nucleotides from the mRNA cap site) and DNA sequences extending through the skeletal 5' noncoding leader, first intron and up to the initiation of translation ATG, converted to a Nco I cloning site at +196, was liberated from a M13 double stranded DNA by Xba I and NcoI digestion, Klenow filled in and then linked into the XbaI and blunt SmaI sites of pbluescript II KS (Stratagene). The NCoI site is regenerated by this cloning step. The 3' UTR and NCR on the 2.3 kb NaeI/HindIII fragment were directionally cloned into a blunt EcoRV site and the adjacent HindIII site of the pBluescript II YS vector cassette. The EcoRV and NaeI sites are destroyed. The restored Nco I site was used to insert cDNA sequences encoding polypeptides. Another cloning vector was constructed by inserting the skeletal alpha actin promoter from −411 to −11 adjacent to the 3' UTR and NCR. This myogenic vector eliminates the first intron and the skeletal actin 5' leader sequence.

These two vectors were used in preparing DNA constructs to test the efficacy of the 3' UTR and NCR.

EXAMPLE 2

Construction of a MVS Containing the Human IGF-I

Figure 4:
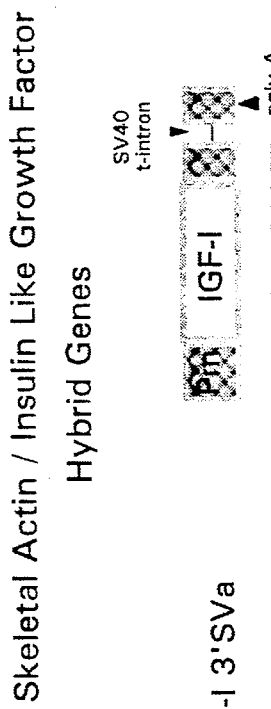
FIG. 4 is a schematic diagram of skeletal alpha actin-/insulin like growth factor-I hybrid genes

Constructions containing the skeletal actin promoter were linked to the human IGF-I EDNA by standard recombinant DNA techniques. Maniatis, Fritsch and Sambrook, Molecular Cloning. A laboratory manual. Cold Spring Harbor Laboratory, Cold Spring Harbor, N.Y., 1982. Examples of a generalized MVS structure is shown in FIG. 3. Specific construction IGF-I are shown in FIG. 4. The construction was made so that the SV40 poly A addition site and the small t-intron were linked to the 3' untranslated region of the IGF-I cDNA. The SV40 sequences were added to increase the stability of nuclear IGF-I RNA transcripts. Since the SV40-t-intron might not be entirely suitable in the expression of IGF-I in muscle cells, five other vectors were made. The SK733 NcoI vector contains approximately 411 nucleotides of the skeletal alpha actin promoter, the natural cap site, 5' untranslated leader and the first intron. An NcoI site was engineered to create a unique insertion cloning site for the cassette containing the IGF-I EDNA, in which the initiation ATG was also converted to an NcoI site. The SK733IGF-I construction utilizes its own poly A site. An NaeI/HindIII fragment which incorporated the skeletal alpha actin 3' untranslated region, poly A addition site, and terminating sequences was linked to SK202, SK733 NcoI, IGF-I and to SK733IGF-I which the IGF-I poly A site was deleted and replaced by that of skeletal alpha actin. In this way IGF-I RNA transcripts containing the skeletal alpha actin 3' untranslated region are stabilized and accumulate in skeletal muscle cells. In addition, by providing contiguous 3' noncoding DNA, IGF-I is buffered against outside genomic sequences and is thus more protected from position effects, when integrated into the genome. In addition, by providing natural terminating sequences, the additional regulatory sequences that mark the transcriptional domain of skeletal alpha actin improve tissue specificity, developmental timing and transcriptional activity.

EXAMPLE 3

Actively of MVS Constructs

To determine the efficacy of actin promoter/gene IGF-I hybrid genes in mouse myogenic cells the MVS was studied using these genes in the background of mammalian $C_2C_{12}$ myoblasts by making a population of stable transfected $C_2C_{12}$ myoblasts. The altered IGF-I expression levels were directly evaluated in these stable myoblast cell lines. Each IGF-I construction (FIG. 4) was co-transfected with the drug selectable vector EMSV-Hygromycin into mouse $C_2C_{12}$ cells. After two weeks of selection, a population of stable myoblasts was selected. A population of $C_2C_{12}$ myoblasts stably transfected only with EMSV-Hygromycin served as the controls. Visual inspection of the transfected myoblast revealed several insights into the role of IGF-I on muscle cell differentiation that would not be obvious in transgenic mice. In general all of the myogenic cell lines containing IGF-I genes caused myoblasts in growth media (10% fetal calf serum) to replicate more extensively than controls. Changing culture medium to 2% horse serum initiates the differentiation process. In the process, control $C_2C_{12}$ myoblasts fuse to form multinucleated myotubes over a period of four days. At the same cell density per culture dish, myoblasts containing SK733IGF-I, SK202IGF-I-SK, SK733IGF-I-SK1 and SK733IGF-I-SK2 fused at least two-to-three days earlier than $C_2C_{12}$ or EMSV-Hygromycin control myoblasts.

Figure 5:
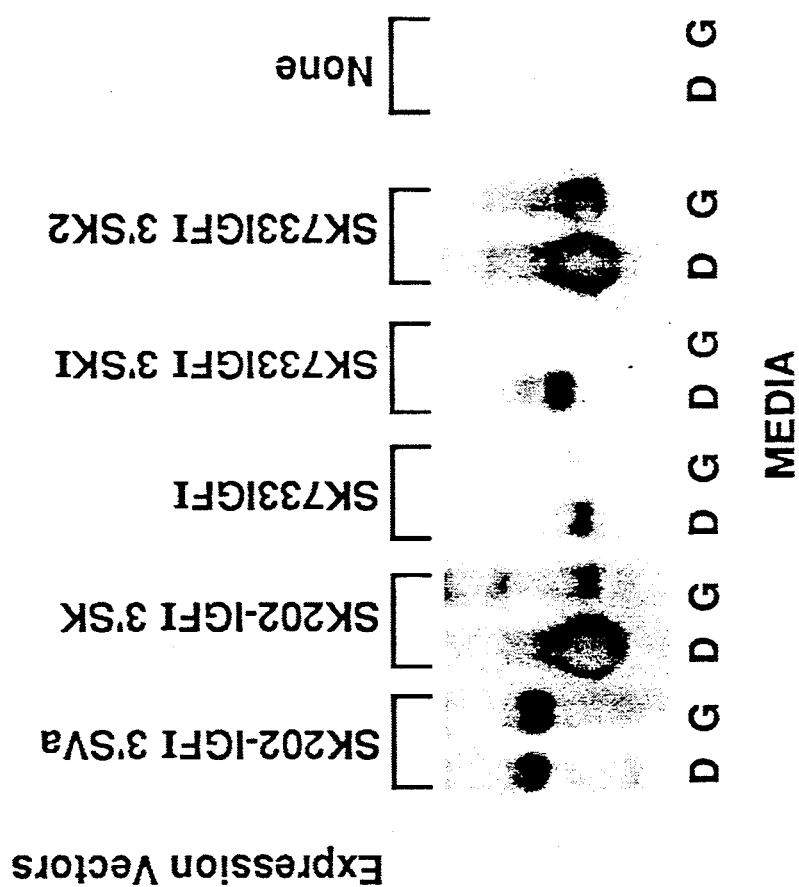
FIG. 5 illustrates the increased activity of the myogenic IGF-I hybrid vectors containing the skeletal alpha actin 3' untranslated region and contiguous non-coding region by the accumulation of IGF-I RNA in stably transfected $C_2C_{12}$ myoblasts.

FIG. 5 shows the steady state accumulation of IGF-I MRNA in $C_2C_{12}$ myoblasts. Equal amounts of total cellular RNA was isolated from stably transfected $C_2C_{12}$ myoblasts grown in growth media (G) or differentiation media (D). The RNA was electrophoretically separated on denaturing agarose gels, transferred onto nylon filters and probed with uniformly $^{32}P$ labeled full length human IGF-I cDNA under standard hybridization techniques. The intensity of the autoradiographic signal on X-ray film provides a relative measure of MRNA accumulation, an overall index of combined transcriptional activity and MRNA stability of the myogenic expression vector system. The IGF-I MRNA in vector, SK202IGF-I-3'SVa did not accumulate in myotubes above myoblast levels. This is a typical expression activity. The SK733IGF-I vector contains the IGF-I 3' untranslated region. The IGF-I MRNA from this vector accumulated in myotubes but at levels substantially lower than SK202IGF-I-SK or SK733IGF-I-SK2. These later two vectors contain the skeletal actin 3' UTR and contiguous noncoding regions. Since, the primary difference in these vectors is the 3' UTR, the increased stabilization of the MRNA transcripts due to the skeletal 3' UTR accounts for about a 100 fold difference in MRNA content.

EXAMPLE 4

Measurement of Secreted Levels of IGF-I from MVS

Differentiated myotube cultures were grown in minimal media (DMEM and 0.05% bovine serum albumin RIA grade) in order to measure the amount of IGF-I synthesized and secreted into the media. SK733IGF-I-SK2 is the most effective construction to express IGF-I in muscle cells. IGF-I was assayed by both radioimmunoassays of tissue culture media and by immunoperoxidase staining of cells. We have found increased levels of IGF-I during the fusion of several of our muscle cultures. The comparison of levels from different MVS are shown in Table 1. In control cultures, the level of IGF-I was in the range of 0.2-0.5 ng/ml. In comparison, vector SK733IGF-I-SK2 has levels of IGF-I at least one hundred times greater.

TABLE I

| IGF-I-Levels in Stably Transfected $C_2C_{12}$ Myoblasts | |
|---|---|
| Construction | IGF-I (ng/ml of media/4 days) |
| SK202IGF-I-3'Sva | 4.4 |
| SK733IGF-I | 3.8 |
| SK733IGF-I-SK2 | 79.0 |
| Control $C_2C_{12}$ | 0.5 |

In a similar manner, immunoperoxidase staining of myogenic cultures revealed the increased production of immunological reactive IGF-I in stable transfected myoblasts but not in the control EMSV-Hygromycin transfected myoblasts or in perfusion $C_2C_{12}$ cells. Antibodies against the A and D regions were used at dilutions of 1:1000. All of the transfected lines including SK202IGF-I were positively immunoperoxidase stained. Thus, it is clear that enhanced levels of IGF-I are being synthesized and exported from the stable myoblasts.

EXAMPLE 5

Insertion of MVS into Transgenic Mice

Figure 6:
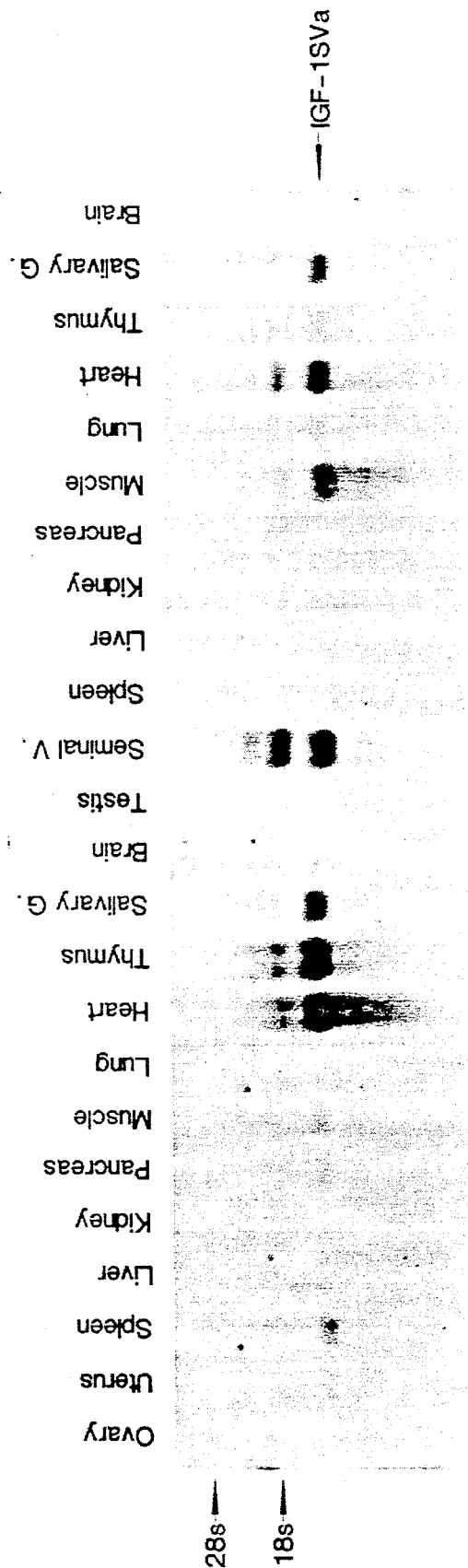
FIG. 6 shows the accumulation of IGF-I RNA in transgenic mouse lines generated with SK202IGF-I-3'SVa myogenic expression vector.
Figure 7:
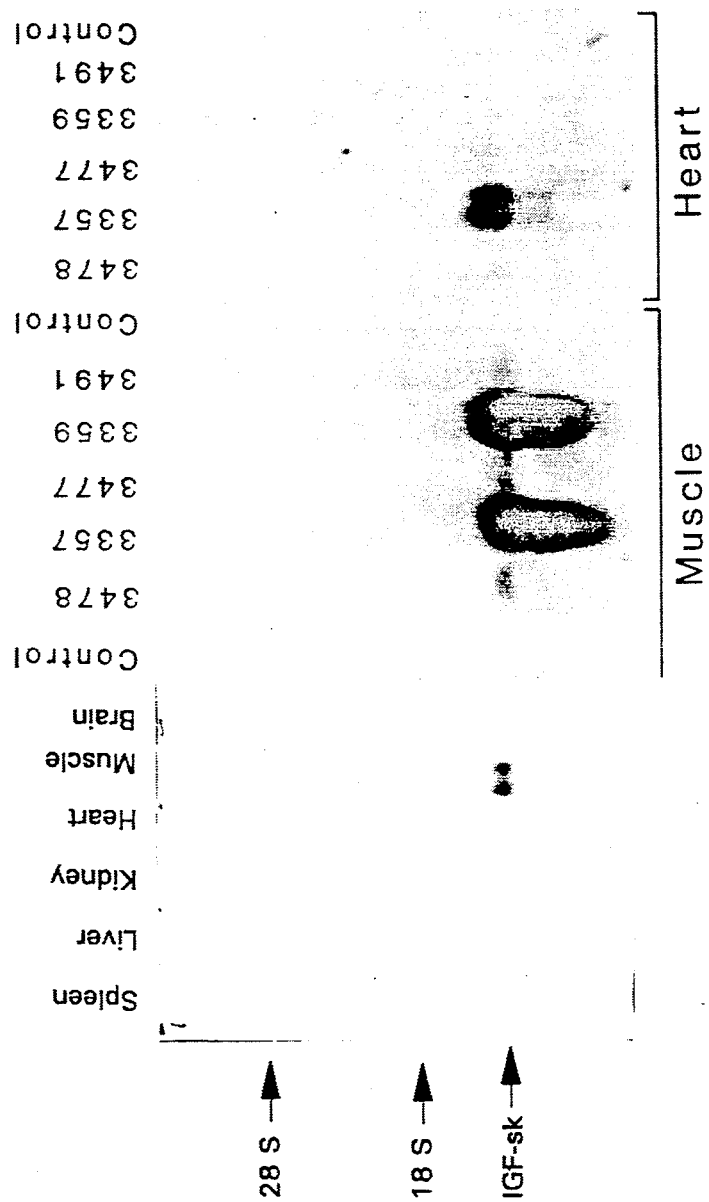
FIG. 7 shows the accumulation of IGF-I RNA in transgenic mouse lines generated with SK202IGF-I-3'SK myogenic expression vector.

Transgenic mice carrying SK202IGF-I-3'SVa or SK202IGF-I-SK were generated by standard oocyte injection (Brinster, et al, Proc. Natl. Acad. Sci. USA Vol 82:4438-4442 (1958)) and bred to demonstrate stable transmission of transgenes to subsequent generations. Transgenics were identified by polymerase chain reaction or Southern genomic DNA blotting analysis from tail cut DNA. Transgenics were tested for muscle specific expression of the transferred IGF-I vector by RNA blotting of total RNA isolated from several tissues as shown in FIGS. 6 and 7. Independent transgenic mouse lines 5484, 5496, 5832, 5834 were generated with SK202IGF-I-3'SVa, containing the SV40 3' intron and poly A addition sequence. Mice from these strains were found to have weak expression primarily in heart tissue, but very low levels were found in skeletal muscle and non-myogenic tissues such as the kidney and brain (FIG. 6). Independent transgenic mouse lines 3357, 3359 were generated with SK733IGF-I-3'SK2. Mice from these strains were found to have elevated expression levels of IGF-I (FIG. 7). These levels are comparable to the endogenous mouse alpha actin gene activity. These levels from SK733IGF-I-3'SK2 show at least 100-1000 fold greater accumulation of IGF-I mRNA in comparison to the levels produced by the SK202IGF-I-3'SVa vector. The addition of the skeletal alpha actin 3'UTR and contiguous noncoding regions allowed for a preferential increase in IGF-I RNA in skeletal muscle rather than cardiac. Thus, the 3' UTR and NCR of the skeletal actin have an important role in enhancing muscle specific gene expression.

EXAMPLE 6

Expression of MVS into Intact Muscle

Intact plasmid DNA in a sterile 20% sucrose solution (wt/Vol) can be injected into mature avian or mammalian muscle. Following a single injection the vector DNA is stable for at least 30 days as a non-integrated extrachromosomal circular DNA in muscle nuclei and, is transcriptionally active. Wolf et al., Science, 247: 1465-1468 (1990). However, greater than 99% of the injected DNA is degraded in muscle under the Wolff protocol (Wolff, et al, BioTechniques Vol. 11:4374-485, 1991). This protocol can be improved by increasing the uptake of plasmid DNA into muscle and reducing vector degradation. The procedure of the present invention uses MVS DNA coated with the relevant transcriptional regulatory factors, the human serum response factor and other human associated nuclear proteins, such as histones, and transcription initiation factors to enhance uptake and stability. The regulatory proteins protect the DNA against muscle nucleases and facilitate the uptake of the protein coated DNA into myogenic nuclei.

The MVS forms a protein/DNA complex by the sequence specific binding of the serum response factor with the inner core $CC(A/T)_6GG$ of the serum response element and by the addition of histones. The interaction with the inner core of the promoter facilitates myogenic cell type restricted expression of the skeletal alpha actin gene. The serum response factor, transcription initiation factor, transregulatory factor and histones are added to the MVS by an in vitro binding reaction to form a reconstituted protein/DNA complex.

One method of post-natal gene therapy involves injecting myogenic vectors into adult muscle for the express purpose of expression of a particular polypeptide. Myogenic vector SK733IGF-I-SK2 was injected at about 100 µg/100 µl into the gastrocnemius muscle of hypophysectomized BALB/C mice. The entire muscle was removed between 1 to 4 weeks following injection and assayed for IGF-I MRNA content in comparison to the uninjected contralateral limb. As compared to controls, tube injected limbs should increase levels of IGF-I MRNA due to the expression of the MVS.

EXAMPLE 7

Treatment with Growth Hormone

Growth hormone is produced and secreted from the anterior pituitary and promotes linear growth in prepuberty children. The secretion of growth hormone is regulated by a stimulatory (growth hormone releasing hormone) and an inhibitory (somatostatin) hypothalamic hormone. Growth hormone acts on the liver and other tissues to stimulate the production of insulin like growth factor I. This factor is responsible for the growth promoting effects of growth hormone. Further, this factor serves as an indicator of overall growth hormone secretion. Serum IGF-I concentration increases in response to endogenous and exogenous administered growth hormone. These concentrations are low in growth hormone deficiency. The injection of a MVS containing the sequence for IGF-I (for example SK 733 IGF-I Sk2) can be used to treat growth disorders. The injection of the MVS is a long-term inexpensive way to increase systemic blood concentration of IGF-I in patients with growth hormone deficiency.

EXAMPLE 8

Treatment of Muscle Atrophy Due To Age

Growth hormone levels decline with increasing age. The levels in healthy men and women above age of 55 are approximately one third lower than the levels in men and women 18 to 33. The decline in growth hormone and IGI-I production correlate with the decrease in muscle mass, termed senile muscle atrophy, and increase in adiposity that occur in healthy human subjects. Administering growth hormone three times a week to healthy 61 to 81 year old men who had serum levels below those of healthy younger men increased the Serum IGF-I levels to within the range found in young healthy adults. This increase level led to increased muscle mass and strength and reduced body fat.

The convenient cloning sites in the Myogenic Vector System are used to construct MVS vectors containing human growth hormone cDNA sequence and/or the human growth hormone releasing (secretory) hormone. The expression of an MVS driven growth hormone gene following intramuscular injections is another way to increase IGF-I serum levels. The MVS expression of the growth factor releasing hormone (GHRH) might be more advantageous than the expression of either IGF-I or the growth hormone vectors transcripts. Since GHRH is reduced in the elderly it appears to be responsible for the lack of GH secretion rather than the anterior pituitary capability of synthesizing growth hormone, thus the increased expression of GHRH from muscle would increase GHRH levels in systemic blood system and can allow for the natural diurnal secretion pattern of GH from the anterior pituitary. In this way, GHRH could act as the natural secretogogue allowing for elevated secretion or release of GH from the hypothalamus of the elderly.

Thus, the application of myogenic vector systems to express insulin-like growth factors through the injection of the SK 733 IGF-I Sk2 vector into adult muscle of the elderly is a long-term inexpensive way to increase systemic blood concentration of IGF-I in the elderly.

EXAMPLE 9

Human Muscle Atrophies Induced by Spinal Cord Injuries, Denervation, and Neuromuscular Diseases Insulin-like growth factors are one of the key factors that potentiate muscle development and muscle growth. Myoblasts naturally secrete IGF-I/IGF-II as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the IGF-I receptor. The receptor is a ligand activated tyrosine specific protein kinase. Insulin-like growth factors are also known neurotrophic agents which maintain neuronal muscular synapses, neuron integrity, and neuronal cell life under neurodegenerative conditions. It has been possible to increase muscle growth under otherwise stringent growth conditions in myogenic cultures and transgenic mice by injecting a MVS containing the IGF-I sequence. The direct injections into adult muscle allows direct transfer of growth promoting gene constructions into muscle and thus provides postnatal gene therapy. Since the MVS driven genes are relatively insensitive to the innervation state of the muscle, they provide a direct and rather broad application for remedying certain kinds of human muscle atrophies caused by spinal cord injuries and neuromuscular diseases. These diseases include the spinal cord muscular atrophies and aymtrophic lateral sclerosis (ALS). In this treatment, the product of the MVS acts as a neurotrophic agent secreted from injected muscle and as a hypertrophic agent to maintain muscle integrity.

EXAMPLE 10

Atheroselerotic Cardiovascular Diseases

Atheroselerotic cardiovascular disease is a major cause of mortality in the United States and the world. The atherosclerotic plaque, the basic underlying lesion in atheroselerosis, contains cholesterol esters that are derived from circulating lipids. These circulating lipids are essential to the development of atheroselerosis. The plasma concentration of high density lipoprotein (HDL) is inversely related to the propensity for developing atherosclerosis. In the nascent state, HDL is secreted in the form of discoidal particles. These particles consist of a bilayer of phosphlipids onto which the apolipoproteins (apoA-I, ApoII and E) are embedded. HDL captures cholesterol esters by the action of an enzyme, lecithin-cholesterol acyltransferase. HDL is secreted from the liver, the small intestine and possibly other tissues.

The APO A-I cDNA is 878 bp and encodes 267 amino acids, including the 24 amino acid propropeptides. Increasing the circulating levels of HDL can influence or reverse cholesterol transport, and thus reduce the propensity for forming atherosclerotic plaques. The insertion of the human APO A-I coding sequences into the MVS serves as an expression vector for enhanced APO A-I expression following injection of plasmid DNA into skeletal muscle. The MVS APO A-I hybrid gene is effective for long term expression, biosynthesis and secretion of HDL in an ectopic site, and thus increases the content of total secretable HDL in blood plasma.

EXAMPLE 11

Vitamin D Regulatable Myogenic Vector System

Figure 8:
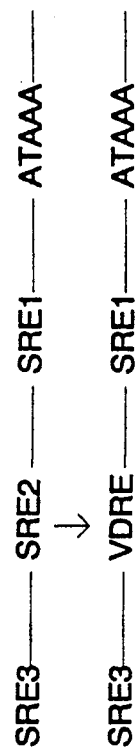
FIG. 8 is a schematic representative of a regulatable MVS using a Vitamin D receptor.

The first tier of myogenic vectors designed with the skeletal actin promoters and 3' untranslated regions provide high levels of unregulated transcriptional activity. Under certain circumstances, it is desirable to control the vector's transcriptional activity and to switch gene transcription on and off by the systemic introduction of a simple inducer or ligand. It is also important that the regulation of the myogenic vector be controlled by natural inducer products that are neither considered toxic to humans nor are immunogenic. Two different Vitamin D regulatory systems are shown in FIGS. 8 and 9.

The cellular concentration of Vitamin D recepter (VDR) in muscle can be increased through the MVS system by injecting a hybrid skeletal actin VDR gene that would be under control of the actin promoter and the 3' UTR stabilizing sequences. The target, SEQ. ID. No. 2, is constructed to contain synthesized multimers of the Vitamin D regulatory element (VDRE). This target is linked to a minimal Herpes Simplex Virus (HSV) thymidine kinase promoter. Transcriptional activity emanating from the TK promoter is regulated by the presence of VDR and coactivated by the ligand, Vitamin D. Any polypeptide sequence cloned in tandem to the HSV promoter, as a EDNA, is driven from the target vector when Vitamin D is introduced into the muscle cells. The hybrid actin VDR gene and the target vector are linked on the same plasmid or coinjected on separate plasmids. Premeasured levels of Vitamin D are administered by drinking a glass of milk or taking a Vitamin D pill. The levels are used to activate transcription of the target vector. Taking the ligand on every other day, will oscillate the promoter activity. Removal of the ligand, Vitamin D, from the diet down regulates or represses transcription from the target vector.

EXAMPLE 12

Vaccine Production

The MVS system is well suited for directing the expression of an exogenous protein epitope in muscle, and thus, for generating vaccines in humans and animals. Targeted sequences are inserted into the cassette of a MVS for expression of protein epitopes for mediating protective immunization. For example, the constant regions of the AIDS viral proteins GP 120, GP 160 and GP 41 and for cell mediated immunity GP 24, the surface proteins of Hepatitis A, B, C, and C viruses, respiratory viruses including influenza, and the gastrointestinal rotoviruses are used. The MVS is then injected into the human or animal.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The myogenic vector systems along with the methods, procedures treatments and vaccinations described herein are presently representative of preferred embodiments are exemplary and not intended as limitations on the scope of the invention. Changes therein and other uses will occur to those skilled in the art which are encompassed within the spirit of the invention or defined by this scope with the claims.

What we claim is:

1. A myogenic vector system (MVS) for the expression of a nucleic acid sequence in myogenic tissue, comprising a promoter; a cassette whose 5' end is attached to the 3' end of the promoter, said cassette containing a nucleic acid sequence which is to be expressed; a myogenic specific 3' untranslated region (3'UTR) and a non-coding region (NCR) contiguous to the 3' end of the 3' UTR, said NCR containing a transcriptional termination signal, wherein the 5' end of the 3' UTR is attached to the 3' end of the cassette.

2. The MVS of claim 1, further comprising a 5' MRNA leader sequence inserted between the promoter and cassette, wherein the 5' end of said leader sequence is attached to the promoter and the 3' end is attached to the cassette.

3. A MVS for the expression of a nucleic acid sequence in myogenic tissues comprising a functional unit which expresses the nucleic acid sequence, wherein the functional unit is comprised of elements all sequentially linked together 5' to 3', said elements include a promoter; a 5' MRNA leader sequence; a first intron; an initiation ATG and NcoI cloning site; a cassette, wherein the cassette has an EcoR1 site at its 3' end and contains the nucleic acid sequence to be expressed; a myogenic specific 3' untranslated region (3' UTR); and a non-coding region (NCR) contiguous to the 3' end of the 3'UTR, said NCR containing a transcriptional termination signal.

4. The MVS of claim 1 or 3, wherein the promoter is myogenic specific.

5. The MVS of claim 2 or 3, wherein the leader sequence is myogenic specific.

6. The MVS of claim 1 or 3, wherein the promoter is selected from the group consisting of skeletal alpha actin gene promoter, fast myosin light chain 1 promoter, myosin heavy chain promoter, tropinin T promoter, muscle creatinine kinase promoter/enhancer, acetycholine receptor subunits, cytomegalovirus promoter, RSV promoter and Rous Sarcoma virus LTR.

7. The MVS of claim 1 or 3, wherein the promoter is a skeletal alpha actin gene promoter.

8. A myogenic vector system (MVS) for the expression of a nucleic acid sequence in myogenic tissue, comprising:

a 5' oligonucleotide, said oligonucleotide including a promoter;

a 3' oligonucleotide containing a myogenic specific 3' untranslated region (3' UTR) and a non-coding region (NCR) contiguous to the 3' end of the 3' UTR, said NCR containing a transcriptional termination signal; and a linker, having a plurality of restriction endonuclease sites, said linker connecting the 5' oligonucleotide to the 3' oligonucleotide and said linker further providing a position for insertion of a cassette containing the nucleic acid to be expressed.

9. The MVS of claim 1, 3 or 8, wherein the 3' UTR and NCR are selected from the group consisting of skeletal alpha actin gene, fast myosin light chain 1 gene, myosin heavy chain gene, tropinin T gene and muscle creatinine kinase gene.

10. The MVS of claim 1, 3 or 8, wherein the 3' UTR and NCR are from a skeletal alpha actin gene.

11. The MVS of claim 1, 3 or 8, further comprising a regulator system for regulating the expression of the nucleic acid sequence.

12. The MVS of claim 10 wherein said regulator system comprising at least one regulatory promoter element which responds to at least one serum response factor and at least one of the serum response factors is a chimera, having its DNA binding domain replaced with a receptor DNA binding sequence.

13. The MVS of claim 12, wherein the receptor binding site of the serum response factor is selected from the family of receptors consisting of vitamin, steroid, thyroid, orphan, hormone, retenoic acid, and thyroxine.

14. The MVS of claim 12, wherein the receptor binding site of the serum response factor is a Vitamin D receptor.

15. The MVS of claim 1, 3 or 8, wherein the expressed nucleic acid sequence codes for a polypeptide.

16. The MVS of claim 1, 3 or 8, wherein the expressed nucleic acid sequence codes for a polypeptide selected from the group consisting of a hormone, growth factor, enzyme, apolipoprotein clotting factor, tumor suppressor, tumor antigen, viral protein, bacterial surface protein, and parasitic cell surface protein.

17. The MVS of claim 1, 3 or 8, wherein the expressed nucleic acid sequence codes for insulin like growth factor I, insulin like growth factor II or insulin growth factor binding protein.

18. The MVS of claim 1, 3 or 8, wherein the expressed nucleic acid sequence codes for growth hormone releasing hormone.

19. The MVS of claim 1, 3 or 8, wherein the expressed nucleic acid sequence codes for apolipoprotein A-I.

20. The MVS of claim 11, wherein the expressed nucleic acid sequence codes for insulin like growth factor I, insulin like growth factor II or insulin growth factor binding protein.

21. The MVS of claim 11, wherein the expressed nucleic acid sequence codes for growth hormone releasing hormone.

22. The MVS of claim 11, wherein the expressed nucleic acid sequence codes for apolipoprotein A-I.

23. A regulatable myogenic vector system (MVS) for the expression of a specific nucleic acid sequence in myogenic tissue comprising:
   a first functional unit, elements of said first unit comprise a myogenic specific promoter; a nucleic acid sequence coding for a receptor; a myogenic specific 3' untranslated region (3' UTR) and a myogenic specific non-coding region (NCR); wherein the elements of the first unit are linked together sequentially starting from the 5' end with the promoter, followed by the receptor nucleic acid sequence, followed by the 3' UTR and contiguous NCR;
   a second functional unit, elements of said second unit comprise a response element corresponding to the receptor; a thymidine kinase promoter; the specific nucleic acid sequence of interest; a myogenic specific 3' UTR and a contiguous myogenic specific NCR; wherein the elements of the second unit are linked together sequentially starting from the 5' end with the response element followed by promoter followed by the specific sequence, followed by the 3' UTR and NCR;
   wherein the first unit expresses the receptor, said receptor forming an interaction between the response element, the receptor and an agent which binds to the receptor, said interaction up regulating the expression of the sequence of interest.

24. The MVS of claim 23 wherein the first and second functional units are on the same vector.

25. The MVS of claim 23, wherein the first and second functional units are on separate vectors.

26. The MVS of claim 23, wherein the receptor is selected from the family of receptors consisting of vitamin, steroid, thyroid, orphan, hormone, retinoic acid and thyroxine.

27. The MVS of claim 23 wherein the receptor is the Vitamin D receptor, the response element is a Vitamin D response element and agent is Vitamin D.

28. The MVS of claim 1, 3 or 23, further comprising a coating, said coating includes:
   a DNA initiation complex, said DNA initiation complex comprises a serum response factor (SRF), a transcription initiation factor (TIF) and a trans-regulatory factor (TRF), wherein the SRF is bound to a serum response element within the promoter, the TIF and TRF interact with the SRF and a TATA box within the promoter to form a stable complex; and
   histones, said histones bound nonspecifically to the remaining DNA in said MVS.

29. The MVS of claim 11, further comprising a coating, said coating including:
   a DNA initiation complex, said DNA initiation complex comprising a serum response factor (SRF), transcription initiation factor (TIF) and a trans-regulatory factor (TRF), wherein the SRF is attached to a serum response element within the promoter, the TIF and TRF interact with the SRF and a TATA box within the promoter to form a stable complex; and
   histones, said histones bound nonspecifically to the remaining DNA in said MVS.

30. The MVS of claim 12, further comprising a coating, said coating includes:
   a DNA initiation complex, said DNA initiation complex comprises a serum response factor (SRF), a transcription initiation factor (TIF) and a trans-regulator factor (TRF), wherein the SRF is attached to a serum response element within the promoter, the TIF and TRF interact with the SRF and a TATA box within the promoter to form a stable complex; and
   histones, said histones bound nonspecifically to the remaining DNA in said MVS.

31. The MVS of claim 8, wherein the 5' oligonucleotide further includes a leader sequence.

32. The MVS of claim 1 or 3, wherein the nucleic acid sequence to be expressed is heterologous relative to the 3' UTR and NCR in the MVS.

* * * * *

UNITED STATES PATENT AND TRADEMARK OFFICE
CERTIFICATE OF CORRECTION

PATENT NO. : 5,298,422

DATED : Mar. 29, 1994

INVENTOR(S) : Robert J. Schwartz, et al

It is certified that error appears in the above-indentified patent and that said Letters Patent is hereby corrected as shown below:

Column 4, line 21, change "1," to -- I, --;

line 23, change "A-1" to -- A-I --;

line 29, change "atheroselerotic" to -- atherosclerotic --.

Column 5, lines 23 and 24, change "transacting" to -- trans-acting --;

line 44, change "MRNA" to -- mRNA --;

line 68, change "MRNA" to -- mRNA -- twice.

Column 6, line 2, change "MRNA" to -- mRNA --;

line 29, change "NWS" to -- MVS --.

Column 8, line 31, change "atheroscierotic" to -- atherosclerotic --.

Column 9, line 22, change "EcoR1" to -- EcoRI --.

Column 10, line 7, change "EDNA" to -- cDNA --;

line 47, change "Actively" to -- Activity --.

Column 11, lines 9, 18, 19, 20, 24, 30 and 32; change "MRNA" to -- mRNA --;

line 52 (Table I), remove the hyphen between "I" and "Levels";

line 55 (Table I), change "Sva" to -- SVa --.

Column 13, lines 11 and 14, change "MRNA" to -- mRNA --.

Column 14, lines 48, 50 and 55; change "atheroselerosis" to -- atherosclerosis --

Column 17, lines 33 and 42, change "MRNA" to -- mRNA --.

UNITED STATES PATENT AND TRADEMARK OFFICE
CERTIFICATE OF CORRECTION

PATENT NO. : 5,298,422

DATED : Mar. 29, 1994

INVENTOR(S) : Robert J. Schwartz, et al

It is certified that error appears in the above-indentified patent and that said Letters Patent is hereby corrected as shown below:

Column 20, line 37, change "regulator" to -- regulatory --.

Signed and Sealed this

Fifth Day of December, 1995

Attest:

BRUCE LEHMAN

Attesting Officer

Commissioner of Patents and Trademarks